US008876900B2

(12) United States Patent
Guederian et al.

(10) Patent No.: US 8,876,900 B2
(45) Date of Patent: Nov. 4, 2014

(54) AC JOINT REPAIR USING SUTURE BUTTON GRAFT CONSTRUCT AND METHOD OF SURGERY

(75) Inventors: Gregory A. Guederian, Naples, FL (US); James J. Guerra, Naples, FL (US)

(73) Assignee: Arthrex, Inc., Naples, FL (US)

(*) Notice: Subject to any disclaimer, the term of this patent is extended or adjusted under 35 U.S.C. 154(b) by 818 days.

(21) Appl. No.: 12/616,062

(22) Filed: Nov. 10, 2009

(65) Prior Publication Data
US 2010/0125297 A1    May 20, 2010

Related U.S. Application Data

(60) Provisional application No. 61/115,425, filed on Nov. 17, 2008.

(51) Int. Cl.
*A61F 2/08* (2006.01)
*A61B 17/04* (2006.01)

(52) U.S. Cl.
CPC ..... *A61B 17/0401* (2013.01); *A61B 2017/0417* (2013.01); *A61B 2017/0404* (2013.01)
USPC .................................. 623/13.14; 623/13.17

(58) Field of Classification Search
CPC ........................................................ A61F 2/08
USPC .............................. 623/13.11–13.14; 128/898
See application file for complete search history.

(56) References Cited

U.S. PATENT DOCUMENTS

| | | | |
|---|---|---|---|
| 6,716,234 B2 | 4/2004 | Grafton et al. | |
| 2007/0179531 A1* | 8/2007 | Thornes | 606/232 |
| 2007/0248638 A1* | 10/2007 | Van Dyke et al. | 424/422 |
| 2008/0027485 A1 | 1/2008 | Jolly et al. | |
| 2008/0234819 A1* | 9/2008 | Schmieding et al. | 623/13.14 |

\* cited by examiner

*Primary Examiner* — David Isabella
*Assistant Examiner* — Jacqueline Woznicki
(74) *Attorney, Agent, or Firm* — Dickstein Shapiro LLP (57) ABSTRACT

Apparatus and methods for fixation of bone to bone, or soft tissue to bone. The apparatus comprises two fixation devices (for example, two buttons) joined by a biologic material (for example, a graft or tendon). Each fixation device is provided with at least one opening that allows the passage of the flexible material attached to the biologic material. The button may be formed, for example, of metal, PEEK or PLLA.

1 Claim, 7 Drawing Sheets

AC JOINT REPAIR USING SUTURE BUTTON GRAFT CONSTRUCT AND METHOD OF SURGERY

CROSS-REFERENCE TO RELATED APPLICATIONS

This application claims the benefit of U.S. Provisional Application No. 61/115,425, filed Nov. 17, 2008, the entire disclosure of which is incorporated by reference herein.

FIELD OF THE INVENTION

The present invention relates to the field of surgery and, more particularly, to a joint or ligament reconstruction technique and associated fixation and reconstruction device.

BACKGROUND OF THE INVENTION

Acromioclavicular ("AC") joint dislocations are characterized by severe upward displacement of the lateral end of the clavicle relative to the acromium of the scapula. Surgery is recommended to reduce and internally fix the displacement, which could otherwise lead to a painful deformity and loss of function.

BRIEF SUMMARY OF THE INVENTION

The present invention provides a technique and reconstruction system for repairing AC joint dislocations. The reconstruction system of the present invention comprises two fixation devices (for example, a button and a washer) joined by a biologic component (for example, a graft such as an allograft or autograft).

The present invention also provides a method of addressing both acute and chronic AC joint indications. The method of the present invention comprises the steps of: (i) providing a surgical construct including at least two fixation devices joined by a biologic component (for example, a graft such as an allograft or autograft); and (ii) engaging the surgical construct in or on the clavicle, and in or on the coracoid.

Other features and advantages of the present invention will become apparent from the following description of the invention which refers to the accompanying drawings.

DETAILED DESCRIPTION OF THE INVENTION

The present invention provides a surgical construct and technique for AC joint dislocation surgical repairs. The surgical construct comprises two fixation devices (for example, a button and a washer, or two buttons have the same or different configuration) joined by a biologic component (for example, a graft such as an allograft or autograft) and at least a strand of flexible material (for example, a high strength suture such as FiberWire® suture, sold by Arthrex, Inc. of Naples, Fla., which is disclosed and claimed in U.S. Pat. No. 6,716,234, the entire disclosure of which is incorporated herein by reference).

Referring now to the drawings, where like elements are designated by like reference numerals, FIGS. 1-4 illustrate various structural elements of surgical construct 100 of the present invention provided with two fixation devices (for example, a button and a washer) and at least one strand of flexible material. FIGS. 5-15 illustrate subsequent steps of an exemplary method of AC joint reconstruction according to an embodiment of the present invention, employing graft system 200 of the present invention that includes the surgical construct 100 of FIGS. 1-4 and a biologic component 50 (for example, a graft) attached to the surgical construct 100.

As illustrated in FIGS. 1-4, surgical construct 100 of the present invention comprises two fixation devices 10, 20 connected by at least one strand of flexible material. In an exemplary embodiment only, the two fixation devices include (i) a first fixation device 10 having a first body provided with a first plurality of apertures and an attachment device (such as a handle) extending about perpendicular to a main surface of the first body; and (ii) a second fixation device 20 having a second body provided with a second plurality of apertures, the second body having a curved orientation relative to the longitudinal axis of the second body.

Figure 1:
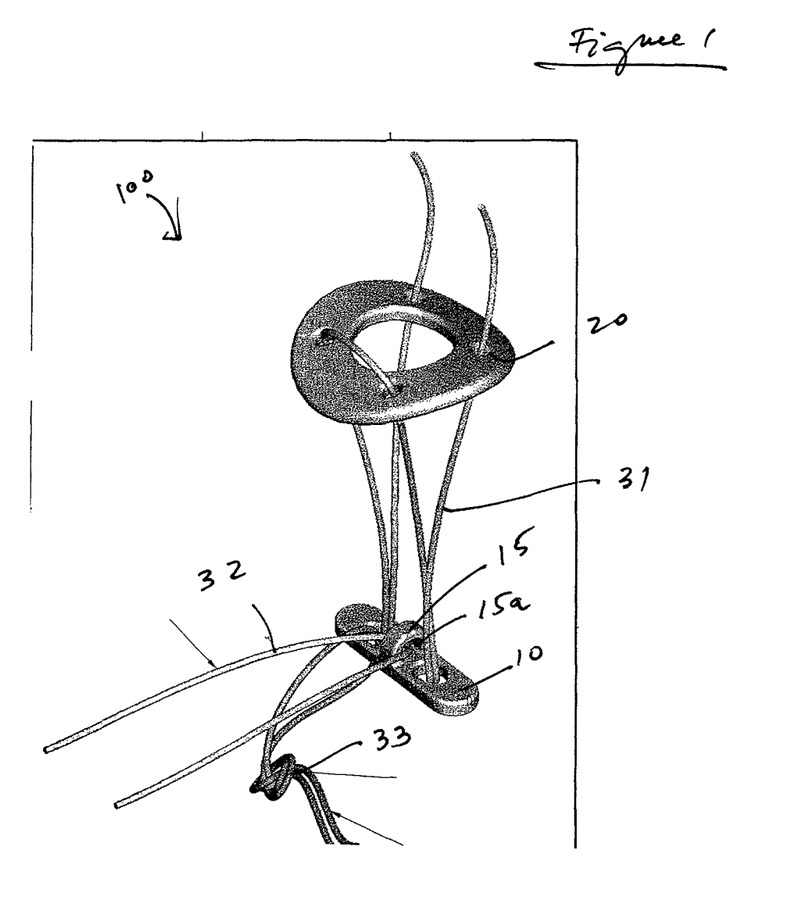
FIG. 1 illustrates a fully assembled view of a surgical construct of the present invention, with three strands of flexible material attached to two fixation devices (such as a button and a washer).
Figure 2A:
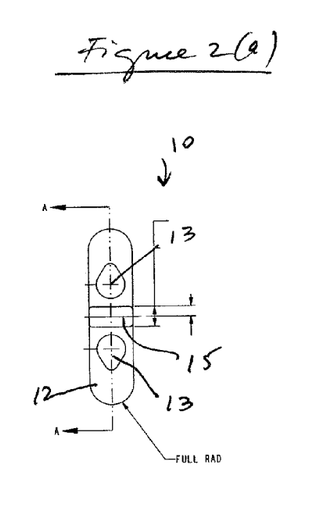
FIG. 2(a) illustrates a top view of the button of the surgical construct of FIG. 1.
Figures 2B, 2C:
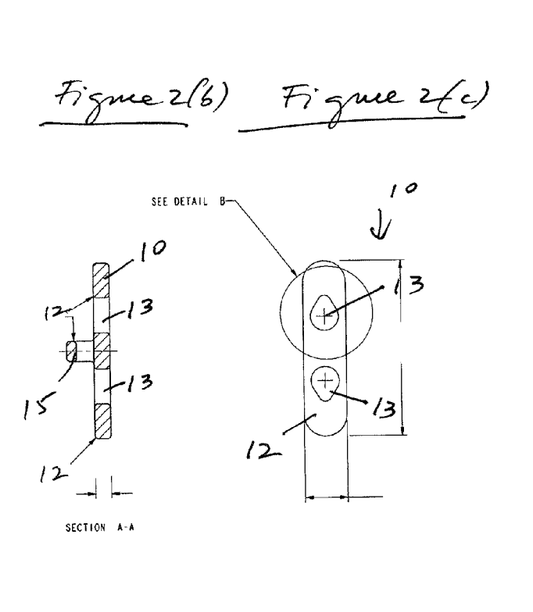
FIG. 2(b) illustrates a side, cross-sectional view of the button of the surgical construct of FIG. 1.
FIG. 2(c) illustrates a bottom view of the button of the surgical construct of FIG. 1.
Figure 2D:
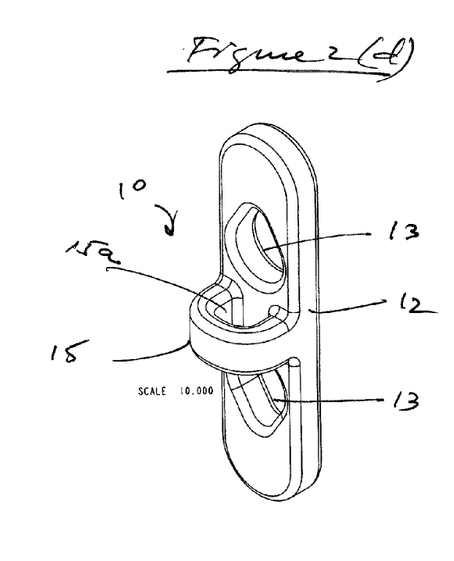
FIG. 2(d) illustrates a perspective view of the button of the surgical construct of FIG. 1.

The first fixation device 10 is illustrated in more details in FIG. 2. As shown in the drawings, and according to an exemplary embodiment only, the first fixation device 10 is a button that comprises a first body 12 provided with a first plurality of apertures 13 and an attachment device (a handle) 15 extending about perpendicular to a main surface of the first body 12. The first plurality of apertures 13 allow at least one flexible strand (for example, suture strands 31, 32, 33 of FIG. 1) to be passed and threaded therethrough (as shown, for example, in FIG. 1 and in the exemplary steps of FIG. 4). Handle 15 of the first fixation device forms opening or aperture 15a (FIG. 2(d)) with body 12 and is configured to allow a biologic construct (for example, a graft such as an allograft or autograft) to be passed therethrough and securely attached to the handle, for further manipulation and insertion through the coracoid and the clavicle.

Figure 3A:
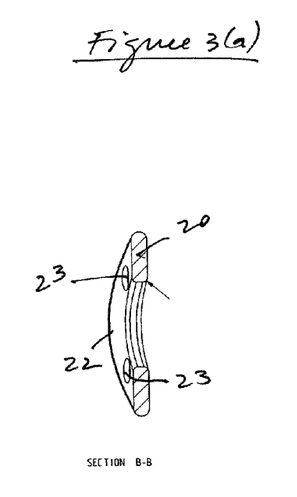
FIG. 3(a) illustrates a cross-sectional view of the washer of the surgical construct of FIG. 1 (taken along line B-B of FIG. 3(b)).
Figures 3B, 3C, 3D, 3E, 3F:
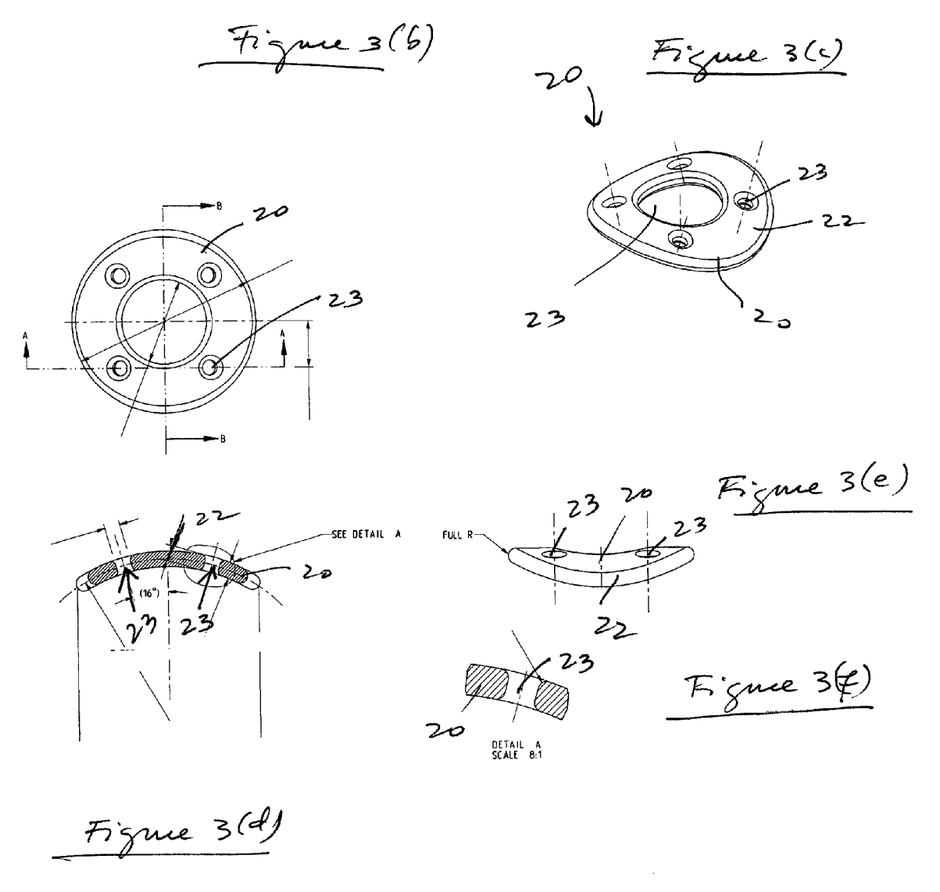
FIG. 3(b) illustrates a top view of the washer of the surgical construct of FIG. 1.
FIG. 3(c) illustrates a perspective, isometric view of the washer of the surgical construct of FIG. 1.
FIG. 3(d) illustrates a cross-sectional view of the washer of the surgical construct of FIG. 1, taken along line A-A of FIG. 3(b).
FIG. 3(e) illustrates a side view of the washer of the surgical construct of FIG. 3(c).
FIG. 3(f) illustrates an enlarged view of the detail A of the washer of FIG. 3(d).
Figure 4A:
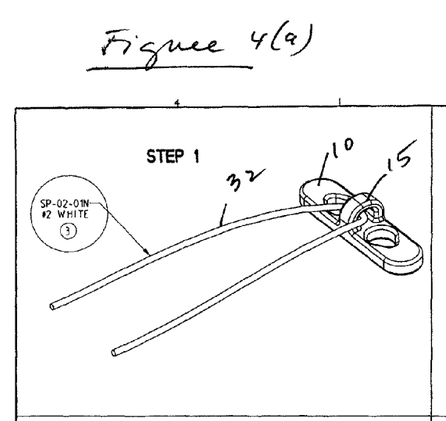
FIGS. 4(a)-(d) illustrate subsequent steps of threading three strands of flexible material through the surgical construct of FIG. 1.
Figure 4B:
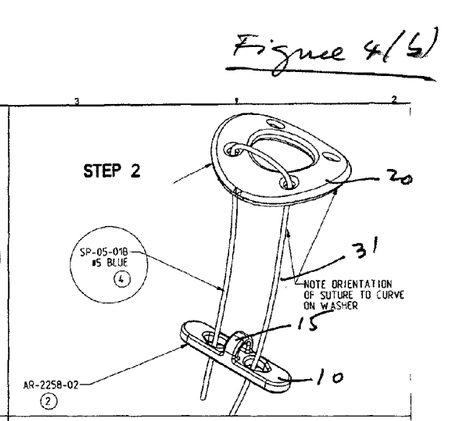
Figure 4C:
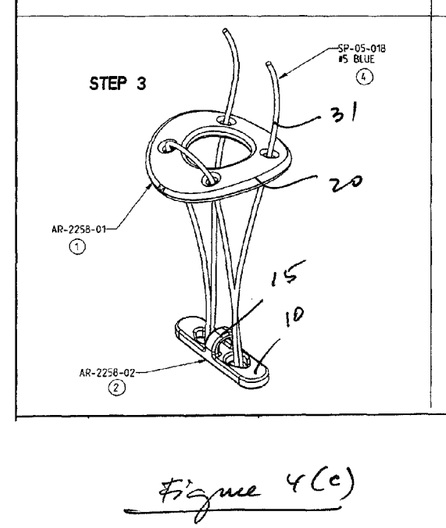
Figure 4D:
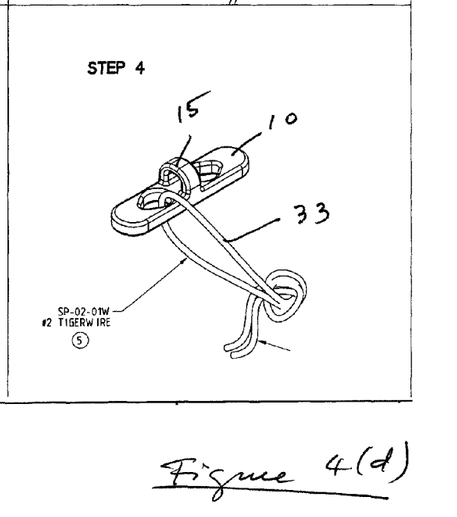

The second fixation device 20 is illustrated in more detail in FIG. 3. As shown in the drawings, and according to an exemplary embodiment only, the second fixation device 20 is a washer that comprises a second body 22 provided with a second plurality of apertures 23. The second plurality of apertures 23 allow at least one flexible strand (for example, suture strands 31, 32, 33 of FIG. 1) to be passed and threaded therethrough (as shown, for example, in FIG. 1 and in the exemplary steps of FIG. 4).

FIGS. 5-15 illustrate subsequent steps of an exemplary method of AC joint reconstruction (stabilization of AC joint dislocation) according to an embodiment of the present invention, employing graft system 200 that includes the surgical construct 100 of FIGS. 1-4 and a biologic component 50 (for example, a graft) attached to the surgical construct 100. The exemplary steps of the AC joint repair illustrated in FIGS. 5-15 will be detailed below with reference to the following description:

The system 200 of the present invention combines strength, simplicity, and a biologic component to address both chronic and acute acromioclavicular joint indications. With system 200 of the present invention, an allograft or autograft is easily secured to the coracoid button 10, and the unique cortical washer 20 allows for fixation of the graft to the clavicle (for example, by screw fixation). The metal clavicle washer 20 and coracoid button 10 are joined by a continuous loop of flexible strand (for example, a #5 FiberWire®), providing fixation during the healing phase. This technique can be completed arthroscopically or open.

Intended Use

The system 200 of the present invention is intended for chronic and acute Grade IV-VI AC separations, as well as Type III separations per surgeon's discretion.

Biologic Compound (Graft) Preparation

A graft 50 (such as an autograft or allograft semitendinosis, gracilis or tibialis) is cleaned and prepared. The graft length is approximately 12-15 cm, to allow the folded graft (as detailed below) to pass through a 4.5-5.5 mm sizing block. Preferably, the graft is whipstitched on each of the free ends, and this can be simplified with a FiberLoop® or TigerLoop™, which is disclosed in U.S. Patent Publication No. 2008/0027485, incorporated by reference herein. In order for there to be whipstitching inside the clavicle tunnel, it is important to begin stitching approximately 30 mm from the graft center point. When doubled over, the graft with whipstitching should easily pass through a 6 mm sizing block.

An exemplary arthroscopic surgical technique employing graft system 200 of the present invention (that includes the surgical construct 100 of FIGS. 1-4 and a biologic component 50 (for example, a graft) attached to the surgical construct 100) is detailed below with reference to FIGS. 5-15. An open surgical technique employing the graft system 200 of the present invention will be detailed following the description of the arthroscopic surgical technique.

Arthroscopic Surgical Technique

The patient is placed in the lateral or beach chair position under a general anesthesia. The arthroscope is introduced into the glenohumeral joint via a standard posterior portal. An anterior portal is created with an outside/in technique using a spinal needle to verify position. A cannula is inserted through the anterior portal. A full radius shaver blade is introduced through the anterior cannula and through the rotator interval. The base of the coracoid is debrided until the coracoid can be visualized. The inferior border of the coracoid is fully exposed using a shaver and a probe. A 70° arthroscope may facilitate visualization and exposure of the coracoid base.

Reference is now made to FIGS. 5-15 and to the following description:

FIG. 5

Figure 5:
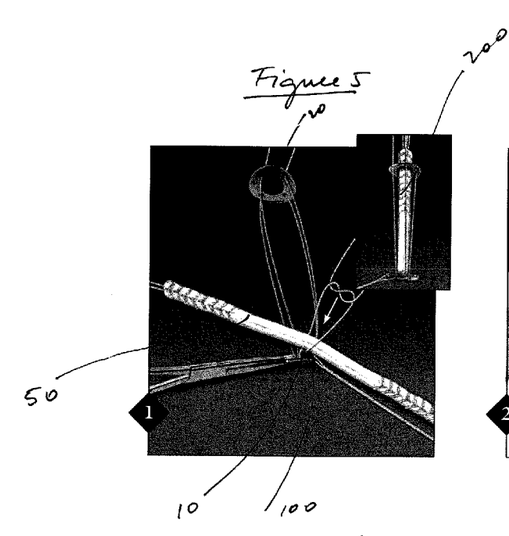
FIGS. 5-15 illustrate subsequent steps of a method of AC joint reconstruction according to an embodiment of the present invention, employing the surgical construct of FIG. 1 and with a biologic component (for example, a graft) attached therein.

The coracoid button 10 and the white FiberWire® suture labeled "Graft" are removed from the package. The midpoint of 12-15 cm allograft or autograft 50 is placed over the "basket handle" 15 of button 10. The graft suture is tied over the graft 50, making sure to tie sufficient half-hitches. The suture is cut leaving a 2 mm tail. The whipstitched sutures and graft limbs are pulled through the clavicle washer 20 to obtain graft/surgical construct 200. Preferably, the graft/construct 200 is kept moist until implanted. The entire construct 200 must pass easily through a 6 mm sizing block.

FIG. 6

Figure 6:
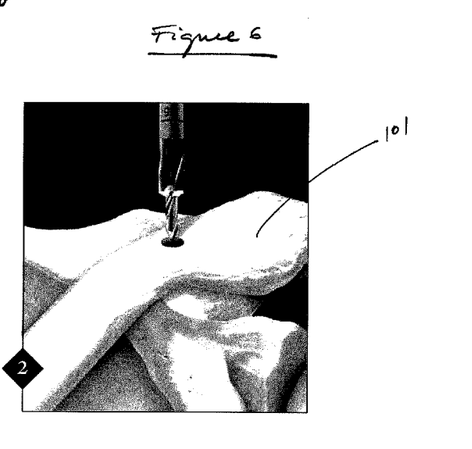

A 2.4 mm unicortical hole is drilled in clavicle 101 at the desired location, which is typically about 35 mm from the distal clavicle 101. The drill hole may be placed in the center of the clavicle 101 in the anterior to posterior plane. The pin is left in place. A 6 mm hole is reamed unicortical over the pin. Both pin and reamer are removed. The hole serves as a pilot hole for AC guide placement.

FIG. 7

Figure 7:
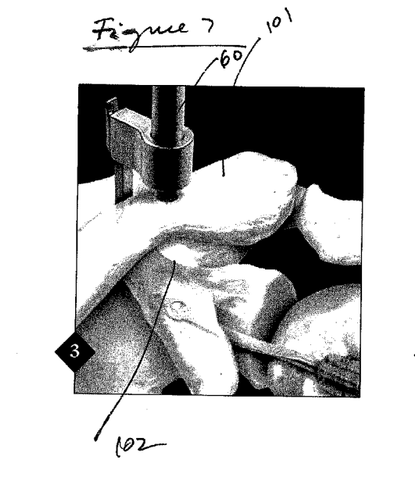

A drill guide 60 is positioned in the previously drilled clavicle pilot hole. The coracoid target is placed on the inferior border of the base of the coracoid 102. The ideal location on the inferior coracoid is close to the base where it projects off of the glenoid. Sufficient bone bridges must be ensured, both anteriorly and posteriorly to the 6 mm reamed tunnel.

FIG. 8

Figure 8:
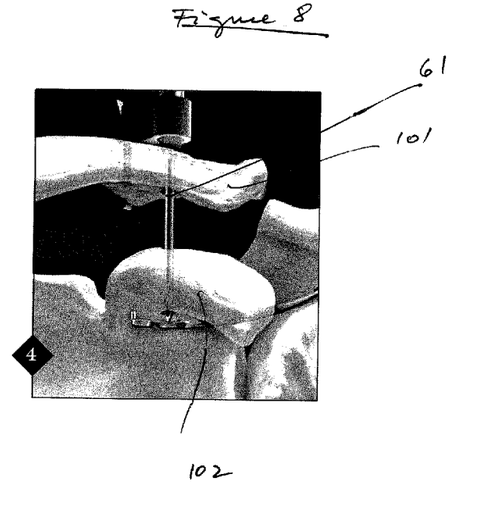

A pin 61 is drilled through the inferior cortex of the clavicle 101 and through the coracoid 102. The pin 61 is left in position.

FIG. 9

Figure 9:
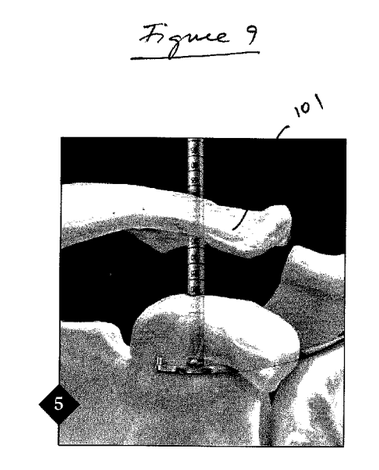

The drill sleeve is removed and the drill guide is repositioned under the pin 61 to keep it from advancing while reaming. Alternatively, the guide can be removed and a curette or open window of a shaver blade can be used to accomplish this step. A 6 mm cannulated reamer is placed over the pin for slow reaming through the clavicle 101 and coracoid 102. The reamer is left, but the inner guide pin is removed.

FIG. 10

Figure 10:
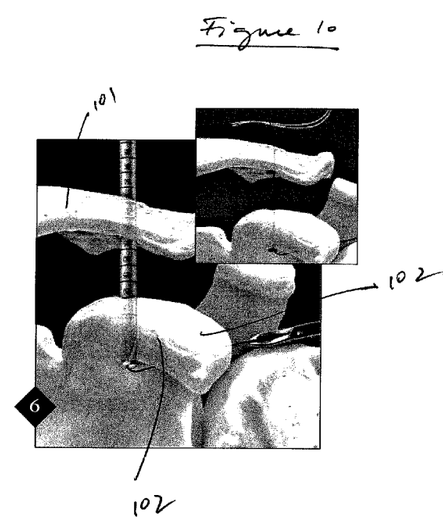

The lasso wire is passed through the reamer, making sure to keep the loop end up. A grasper is used to pull the lasso out of the anterior portal. The cannulated reamer is removed and an end of "Traction" (TigerWire) suture of the GraftRope construct is loaded into the loop (e.g., the lasso loop). The lasso loop is used to draw "Traction" suture through the clavicle 101 and the coracoid 102, and out the anterior portal.

FIG. 11

Figure 11:
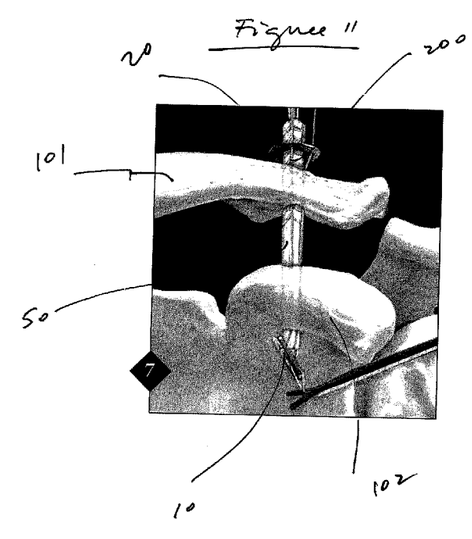

The "Traction" suture is pulled to deliver the coracoid button 10 through the clavicle 20. A forked probe, suture retriever, or knot pusher may be used to leverage the suture beneath the coracoid 102, while pulling on the suture from outside the anterior portal. This facilitates delivery of the coracoid button 10 and graft 50 through the coracoid 102. Once the button 10 is through the coracoid 102, a probe may be used to maneuver the button 10 into the desired position at the coracoid base 102.

FIG. 12

Figure 12:
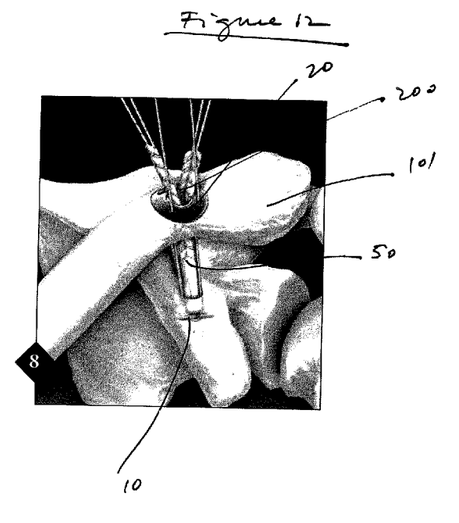

The clavicle is reduced. While the clavicle is maintained reduced, the #5 blue FiberWire is tightened. The index finger may be used to "walk" the clavicle washer 20 to the clavicle 101. The washer 20 is tied down making sure to throw multiple half-hitches. The suture is cut leaving adequate suture tails.

FIG. 13

Figure 13:
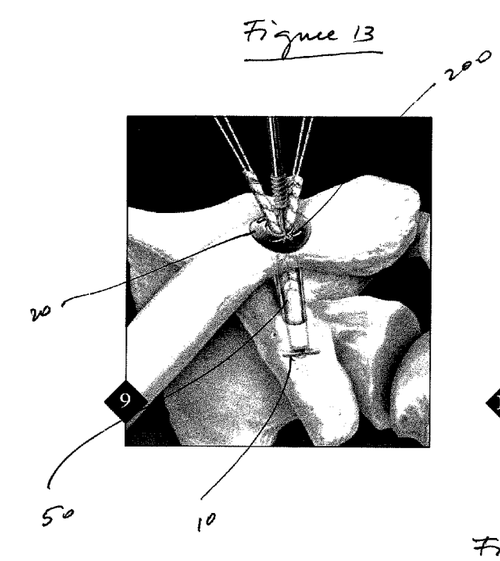
Figure 14:
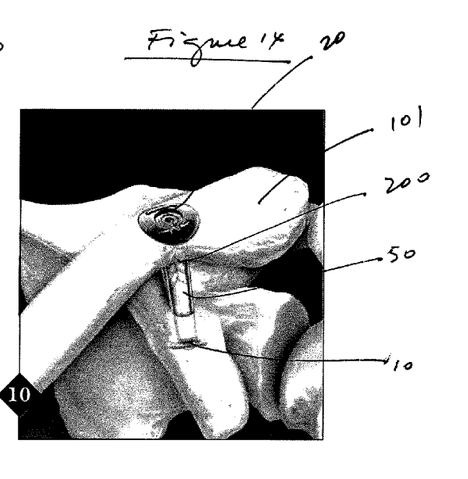
Figure 15:
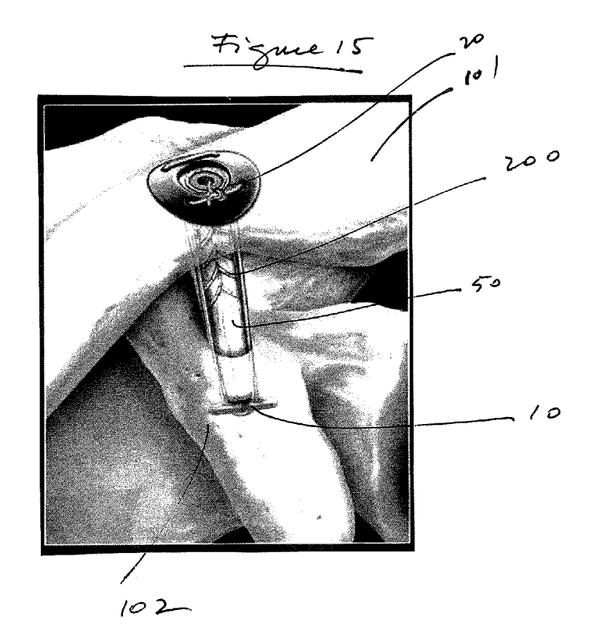

The limbs of the graft 50 are separated, and both limbs are pull tight. A flexible strand (such as a 1.1 mm Nitinol wire) is placed through both cortices of the clavicle tunnel to act as a guide. An interference device (for example, a 5.5 mm Tenodesis Screw) and a driver (for example, a Tenodesis driver) are placed over the guide wire and the screw is inserted until flush.

FIG. 14

For final construct (FIGS. 14 and 15), the graft limbs are cut at screw level. Alternatively, or additionally, the limbs are run to the AC joint and are secured to the capsule with Fiber-Wire, or to the anterior and posterior acromion with fixation devices (such as 3 mm SutureTaks).

Open Surgical Technique

Incision and Exposure

An incision of about 4 cm is performed beginning approximately 3.5 cm proximal to the AC joint and is cut inferiorly toward the coracoid. The deltotrapezial fascia is split longitudinally over the distal clavicle. The deltoid fibers are split inferiorly toward the coracoid. The superior surface of the coracoid is exposed.

Clavicle/Coracoid Tunnel Preparation

A 2.4 mm guide pin is drilled through both cortices of the clavicle, approximately 35 mm proximal to the AC joint. The guide pin is overreamed with a 6 mm reamer to create a bicortical clavicle hole. The guide pin and reamer are removed from the clavicle. Further exposure of the superior surface of the coracoid is conducted. The medial and lateral borders at the base of the projection of the coracoid are defined. Under direct visualization, a 2.4 mm guide pin is drilled through the midpoint of the base of the coracoid. Sufficient bone bridges both medially and laterally to the coracoid tunnel must be left. A bicortical coracoid hole is created with a 6 mm reamer. To protect from advancing the guide pin distally, a retractor is placed under the coracoid. The guide pin and reamer are removed from the coracoid.

Positioning of the Passing Wire

A wire (for example, a SutureLasso™ Wire) is fed through the coracoid graft passing instrument (right or left) which in turn is used to pass the wire through the coracoid tunnel. The wire is retrieved lateral to the conjoined tendon and inferior to the coracoacromial ligament. The coracoid graft passing instrument is removed and the portion of the wire above the coracoid is passed retrograde through the clavicle tunnel.

GraftRope Positioning/Implantation

The end of "Traction" (TigerWire®) suture of the surgical construct 100 is loaded into the lasso loop. The lasso loop is used to draw "Traction" suture through the clavicle and coracoid and inferior to the coracoacromial ligament. The "Traction" suture is pulled to deliver the coracoid button through the clavicle. It may be necessary to use a suture retriever or knot pusher to leverage the "Traction" suture beneath the coracoid, while pulling on the suture. This may facilitate delivery of the coracoid button and graft through the coracoid. Once the button is through the coracoid, a finger may be used to maneuver the button into the desired position at the coracoid base. The clavicle is reduced. While the clavicle is maintained reduced, the #5 blue FiberWire® is tightened. The index finger may be used to "walk" the clavicle washer to the clavicle. The washer is tied down making sure to throw multiple half-hitches and leaving adequate suture tails. The limbs of the graft are separated, and both limbs are pulled tight. A wire (for example, a 1.1 mm Nitinol wire) is pulled through both cortices of the clavicle tunnel to act as a guide. An interference device (for example, a 5.5 mm Tenodesis Screw) and a driver (for example, a Tenodesis driver) are placed over the guide wire and the screw is inserted until flush. For final construct, the graft limbs are cut at screw level, or the limbs may be run to the AC joint and secured to the capsule with FiberWire®, or to the anterior and posterior acromion with fastening devices such as 3 mm SutureTaks®.

If desired, the graft can be passed beneath/around the coracoid instead of tied to the coracoid button. In this case, it is possible to drill a 4 m tunnel to pass the button alone and the graft limbs can be passed through the clavicle tunnel and clavicle washer.

Although the present invention has been described above with reference to a specific embodiment with FiberWire® suture, the invention contemplates any flexible material including hollow braided constructs, or filaments of various colors, among many others.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A method for internal fixation of acromioclavicular joint dislocations, comprising the steps of:
   providing an internal fixation device comprising a first member with an oblong configuration and provided with a plurality of first apertures and an opening; and a second member with a second round configuration and provided with a plurality of second apertures and a central opening; wherein the first and second members allow a graft, tendon or ligament to extend between the first and second members;
   placing a midpoint of the graft, tendon or ligament over the an opening of the first member and, using a suture passed through the opening of the first member, securely attaching the graft, tendon or ligament to the first member;
   pulling the first member with the attached the graft, tendon or ligament through respective holes drilled through a clavicle and a coracoid;
   securing the first member to the coracoids by pivoting the first member after it is passed through the coracoid; and
   separating limbs of the graft, tendon or ligament passing through the hole drilled in the clavicle and through the central opening of the second member, and inserting a screw through the central opening between the limbs to secure the limbs of the graft, tendon or ligament to the clavicle;
   reducing the distance between the clavicle and the coracoid; and
   securing the second member to the clavicle with a suture passing through the second apertures of the second member.

* * * * *